(12) United States Patent
Walston et al.

(10) Patent No.: US 9,615,579 B2
(45) Date of Patent: Apr. 11, 2017

(54) COMPOSITIONS FOR POWDERY MILDEW CONTROL AND METHODS OF THEIR USE

(71) Applicant: Valent U.S.A., Corporation, Walnut Creek, CA (US)

(72) Inventors: Allison Walston, Hood River, OR (US); John Andrew Pawlak, II, Walnut Creek, CA (US)

(73) Assignee: Valent U.S.A. Corporation, Walnut Creek, CA (US)

( * ) Notice: Subject to any disclaimer, the term of this patent is extended or adjusted under 35 U.S.C. 154(b) by 0 days.

(21) Appl. No.: 15/198,623

(22) Filed: Jun. 30, 2016

(65) Prior Publication Data

US 2017/0000125 A1    Jan. 5, 2017

Related U.S. Application Data

(60) Provisional application No. 62/188,279, filed on Jul. 2, 2015.

(51) Int. Cl.
*A01N 43/56* (2006.01)
*C07D 231/14* (2006.01)
*A01N 25/30* (2006.01)
*A01N 43/653* (2006.01)
*A01N 37/50* (2006.01)

(52) U.S. Cl.
CPC ............. *A01N 43/56* (2013.01); *A01N 25/30* (2013.01); *A01N 37/50* (2013.01); *A01N 43/653* (2013.01)

(58) Field of Classification Search
CPC .............................. A01N 43/56; C07D 231/14
USPC ........................................ 514/406; 548/374.1
See application file for complete search history.

(56) References Cited

U.S. PATENT DOCUMENTS 5,093,347 A * 3/1992 Graneto ............... C07D 231/14
514/406

* cited by examiner

*Primary Examiner* — Charanjit Aulakh
(74) *Attorney, Agent, or Firm* — Wood, Phillips, Katz, Clark & Mortimer

(57) ABSTRACT

The present invention relates to compositions and methods for controlling apple powdery mildew comprising treating an apple tree with a silicone containing surfactant and 3-(difluoromethyl)-1-methyl-N-[(3R)-1,1,3-trimethyl-2,3-dihydroinden-4-yl]pyrazole-4-carboxamide.

20 Claims, No Drawings

COMPOSITIONS FOR POWDERY MILDEW CONTROL AND METHODS OF THEIR USE

FIELD OF THE INVENTION

The present invention generally relates compositions and methods for controlling apple powdery mildew comprising applying a silicone containing surfactant and an effective amount of 3-(difluoromethyl)-1-methyl-N-[(3R)-1,1,3-trimethyl-2,3-dihydroinden-4-yl]pyrazole-4-carboxamide to an apple tree.

BACKGROUND OF THE INVENTION

Apple powdery mildew, caused by *Podosphaera leucotricha* is a major problem for growers of apple trees. Apple powdery mildew is present in all apple producing areas of the world. Apple powdery mildew causes symptoms on young shoots, leaves, blossoms and fruit. The fungus reduces tree vigor, flower bud production and fruit quality.

There are generally two phases to apple powdery mildew infection. The fungus overwinters in dormant flower and shoot buds that were infected the previous year. As the temperatures warm, the fungus and buds break dormancy and the fungus infects the new growth. Conidia are released from the new growth and the spores cause secondary infections where they land.

Currently, it is very difficult to control apple powdery mildew for several reasons. First, *Podosphaera leucotricha* has developed resistance to some fungicides. Secondly, some effective fungicides are being banned in some areas because they are harmful to the environment or humans.

Yet another issue is that often the currently available treatments have to be applied repeatedly to be effective and to treat secondary infections. Some apple orchards are treated with fungicides for apple powdery mildew up to 12 times in a growing season. The extra applications add to the expense of the treatment because more of the product must be purchased, and significant time and labor resources are used during the subsequent applications. Further, each new application increases the risk of exposure of the product to non-target trees.

Other means of treating trees are available but have proven to be ineffective or impractical to implement. Some methods require professionals who are trained in specialized equipment to apply the product. Other expensive methods include invasive drilling, bark injections, or high-pressure root flare injections. For example, there was a fungicide that provided some systemic fungal protection, however, it was effective only when injected directly into the tree.

Non-chemical treatments such as waxes and oils have also been used, but they provide inconsistent results. Manually removing the infected material from trees is extremely expensive and not practical for large orchards.

Therefore, there is a need in the art for safe and effective methods for providing long-term protection to apple trees from apple powdery mildew infection.

SUMMARY OF THE INVENTION

The present invention is directed compositions and methods for controlling apple powdery mildew comprising applying an effective amount of 3-(difluoromethyl)-1-methyl-N-[(3R)-1,1,3-trimethyl-2,3-dihydroinden-4-yl] pyrazole-4-carboxamide and a silicone containing surfactant to an apple tree.

DETAILED DESCRIPTION OF THE INVENTION

Applicant unexpectedly found that 3-(difluoromethyl)-1-methyl-N-[(3R)-1,1,3-trimethyl-2,3-dihydroinden-4-yl] pyrazole-4-carboxamide provided excellent apple powdery mildew control when 3-(difluoromethyl)-1-methyl-N-[(3R)-1,1,3-trimethyl-2,3-dihydroinden-4-yl]pyrazole-4-carboxamide was combined with a silicone containing surfactant. This was unexpected because other surfactants when combined with 3-(difluoromethyl)-1-methyl-N-[(3R)-1,1,3-trimethyl-2,3-dihydroinden-4-yl]pyrazole-4-carboxamide, and 3-(difluoromethyl)-1-methyl-N-[(3R)-1,1,3-trimethyl-2,3-dihydroinden-4-yl]pyrazole-4-carboxamide alone, failed to provide adequate powdery mildew control. Further, 3-(difluoromethyl)-1-methyl-N-[(3R)-1,1,3-trimethyl-2,3-dihydroinden-4-yl]pyrazole-4-carboxamide when combined with a silicone containing surfactant was capable of providing control of powdery mildew that was superior to commercially available formulations at much lower rates (i.e. fewer grams per hectare) than the commercially available formulations.

3-(Difluoromethyl)-1-methyl-N-[(3R)-1,1,3-trimethyl-2,3-dihydroinden-4-yl]pyrazole-4-carboxamide has the following structure:

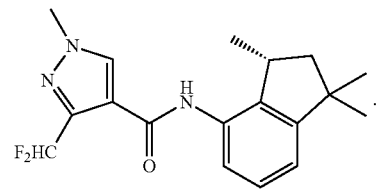 [SMILES: C[C@@H]1CC(C)(C)c2cccc(NC(=O)c3cn(C)nc3C(F)F)c21]

In an embodiment, the present invention is directed to methods for controlling apple powdery mildew comprising applying an effective amount of 3-(difluoromethyl)-1-methyl-N-[(3R)-1,1,3-trimethyl-2,3-dihydroinden-4-yl] pyrazole-4-carboxamide and a silicone containing surfactant to an apple tree.

In an embodiment, the effective amount of 3-(difluoromethyl)-1-methyl-N-[(3R)-1,1,3-trimethyl-2,3-dihydroinden-4-yl]pyrazole-4-carboxamide is from about 0.0001 to about 1,000 grams per hectare. In a preferred embodiment, the effective amount of 3-(difluoromethyl)-1-methyl-N-[(3R)-1,1,3-trimethyl-2,3-dihydroinden-4-yl]pyrazole-4-carboxamide is from about 0.001 to about 250 grams per hectare. In a more preferred embodiment, the effective amount of 3-(difluoromethyl)-1-methyl-N-[(3R)-1,1,3-trimethyl-2,3-dihydroinden-4-yl]pyrazole-4-carboxamide is from about 1 to about 150 grams per hectare. In a most preferred embodiment, the effective amount of 3-(difluoromethyl)-1-methyl-N-[(3R)-1,1,3-trimethyl-2,3-dihydroinden-4-yl]pyrazole-4-carboxamide is from about 25 to about 75 grams per hectare.

Suitable surfactants are those that include silicone. As used herein "silicone containing surfactants" refer to surfactants that include silicone. Examples of suitable surfactants include, but are not limited to: a mixture of 3-(3-hydroxypropyl)-heptamethyltrisiloxane-ethoxylated acetate, polyethylene glycol monallyl acetate and polyethylene glycol diacetate; modified polytrisiloxanes; polyalkyleneoxide modified heptamethyltrisiloxanes; a mixture of silicone-polyether copolymers, propylene glycol, and dimethylpolysiloxane; alcohol ethoxylates; polyether-polymethylsiloxane-copolymer and polyether; and combinations thereof. One presently preferred surfactant is a mixture of 3-(3-hydroxypropyl)-heptamethyltrisiloxane-ethoxylated acetate, polyethylene glycol monallyl acetate and polyethylene glycol diacetate. Other suitable silicone surfactants can be found in, for example, McCutcheon's volume 2: Functional Materials, North American Edition, 2013.

In an embodiment, from about 100 to about 1,000 milliliters per hectare of silicone containing surfactant is applied.

In a preferred embodiment, from about 250 to about 750 milliliters per hectare of silicone containing surfactant is applied. In a more preferred embodiment, from about 500 to about 650 milliliters per hectare of silicone containing surfactant is applied.

The rates of application listed herein are based a formulation containing 100% surfactants. It is within the skill of one in the art to adjust the amount/volume of silicone containing surfactant based on the purity of the silicone containing surfactant formulation.

Suitable apple tree varieties include, but are not limited to, braeburn, cameo, cortland, crabapple, empire, Fuji, flowering crabapple, gala, ginger gold, golden delicious, granny smith, idared, honeycrisp, jonagold, jonathan, McIntosh, mutsu, nittany, pink lady, rome, rome beauty, red delicious, stayman, winesap, and york. In a preferred embodiment, the apple tree varieties are selected from the group consisting of cortland, empire, ginger gold, golden delicious, flowering crabapple, granny smith, idared, jonathan, McIntosh, and rome beauty. In a more preferred embodiment, the apples are cortland or jonagold.

In embodiments of the present invention, the apple trees may be sprayed with high pressure or low pressure (meaning lower than 40 psi) spraying mechanisms. Suitable ranges of pressure include from about 30 to about 100 psi. A backpack sprayer, airblast sprayer, or similar sprayer can be used for ease of the person delivering the spray to the tree.

In another embodiment, the treatments may be applied more than one time per season. In a preferred embodiment, the treatments are applied 2 to 10 times per season. In a more preferred embodiment, the treatments are applied 3 to 7 times per season.

If the treatments are applied more than once per season, the treatments may be applied 1 to 30 days apart. In a preferred embodiment, the treatments are applied 5 to 20 days apart. In a more preferred embodiment, the treatments are applied 7 to 14 days apart.

The treatments may be applied to the trees during the time period beginning when foliage is first visible and ending when the fruit is ready for harvest. In a preferred embodiment, the treatments may applied to the trees during the time period beginning when the flower buds are visible and ending when the fruit is greater than 10 millimeters ("mm") in diameter.

In yet another embodiment, the 3-(difluoromethyl)-1-methyl-N-[(3R)-1,1,3-trimethyl-2,3-dihydroinden-4-yl]pyrazole-4-carboxamide and the silicone containing surfactant may be mixed with a solvent prior to application. One presently preferred solvent is water.

In a preferred embodiment, the effective amount of 3-(difluoromethyl)-1-methyl-N-[(3R)-1,1,3-trimethyl-2,3-dihydroinden-4-yl]pyrazole-4-carboxamide is from about 10 to about 1,000 parts per million active ingredient solution concentration. In a more preferred embodiment, the effective amount of 3-(difluoromethyl)-1-methyl-N-[(3R)-1,1,3-trimethyl-2,3-dihydroinden-4-yl]pyrazole-4-carboxamide is from about 10 to about 500 parts per million active ingredient solution concentration. In an even more preferred embodiment, the effective amount of 3-(difluoromethyl)-1-methyl-N-[(3R)-1,1,3-trimethyl-2,3-dihydroinden-4-yl]pyrazole-4-carboxamide is from about 10 to about 200 parts per million active ingredient solution concentration. In a most preferred embodiment, the effective amount of 3-(difluoromethyl)-1-methyl-N-[(3R)-1,1,3-trimethyl-2,3-dihydroinden-4-yl]pyrazole-4-carboxamide is from about 13 to about 80 parts per million active ingredient solution concentration.

In an embodiment, the present invention is directed a composition for controlling apple powdery mildew comprising from about 0.00027% to about 0.0007% v/v of a silicone containing surfactant, about 0.000013% to about 0.00008% w/v 3-(difluoromethyl)-1-methyl-N-[(3R)-1,1,3-trimethyl-2,3-dihydroinden-4-yl]pyrazole-4-carboxamide and from about 99.99922% to about 99.99972% v/v water.

In an embodiment, 3-(difluoromethyl)-1-methyl-N-[(3R)-1,1,3-trimethyl-2,3-dihydroinden-4-yl]pyrazole-4-carboxamide and the silicone containing surfactant may be mixed with another fungicide. In a preferred embodiment, the fungicide is a triazole fungicide. Two presently preferred triazole fungicides are metconazole and propiconazole.

In another preferred embodiment, 3-(difluoromethyl)-1-methyl-N-[(3R)-1,1,3-trimethyl-2,3-dihydroinden-4-yl]pyrazole-4-carboxamide and the silicone containing surfactant may be mixed with a phosphonate fungicide. In a preferred embodiment, the phosphonate fungicide comprises mono and dipotassium salts of phosphorous acid (for example, Agri-Fos®, AgriFos is available from and a registred trademark of AgBio).

In a further embodiment, 3-(difluoromethyl)-1-methyl-N-[(3R)-1,1,3-trimethyl-2,3-dihydroinden-4-yl]pyrazole-4-carboxamide and the silicone containing surfactant may be mixed with an inhibitor of succinate-dehydrogenase. Preferably, the inhibitor of succinate-dehydrogenase is selected from the group consisting of penflufen, isopyrazam, benzovindiflupyr, bixafen, sedaxane, fluxapyroxad, fluopyram, penthiopyrad, boscalid, N-[1-(2,4-dichlohenyl)-1-methoxypropan-2-yl]-3-(difluoromethyl)-1-methyl-1H-pyrazole-4-carboxamide, N[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(dichlormethylen)-1,2,3,4-tetrahydro-1,4-methanonaphthalen-5-yl]-3-(difluormethyl)-1-methyl-1H-pyrazol-4-carboxamid.

In an embodiment, 3-(difluoromethyl)-1-methyl-N-[(3R)-1,1,3-trimethyl-2,3-dihydroinden-4-yl]pyrazole-4-carboxamide and the silicone containing surfactant may be mixed with an insecticide. One preferred class of insecticides is neonicotinoids. More preferably, the neonicotinoid is selected from the group consisting of clothianidin, imidacloprid, thiacloprid, dinotefuran, acetamiprid, nitenpyram and thiamethoxam.

In a further embodiment, 3-(difluoromethyl)-1-methyl-N-[(3R)-1,1,3-trimethyl-2,3-dihydroinden-4-yl]pyrazole-4-carboxamide is mixed with a strobilurin. Preferably, the strobilurin is selected from the group consisting of picoxystrobin, pyraclostrobin, dimoxystrobin, metominostrobin, azoxystrobin, trifloxystrobin, fluoxastrobin, mandestrobin and orysastrobin.

As used herein, "yield" refers to an increase in the amount or number of apples that are marketable.

As used herein, "controlling apple powdery mildew" refers to reducing the amount of damage caused by apple powdery mildew to a level that is acceptable to the grower. For example, "controlling apple powdery mildew" can mean the prevention of the fungal infection, the treatment of an existing infection, limiting the spread of the infection, or the use of the methods as a prophylactic.

Throughout the application, the singular forms "a," "an," and "the" include plural reference unless the context dearly dictates otherwise.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The invention will be understood more clearly from the following non-limiting representative example. Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

EXAMPLES

Example 1

Applicant conducted the following study to determine the effect of 3-(difluoromethyl)-1-methyl-N-[(3R)-1,1,3-trimethyl-2,3-dihydroinden-4-yl]pyrazole-4-carboxamide foliar applications on fungal infections in apple trees.

Apples, jonagold variety, that were about 9 years old were used in this study. The trees were spaced about 3 meters apart in about 5 meter rows. The trees were sprayed with a backpack sprayer with a hollow cone nozzle. About 300 liters per hectare was used for each treatment. The trees were treated five times at 14 day intervals. At the time of treatment, the trees were at the following stages of development: (1) flower buds visible but closed; (2) red bud stage with flower petals; (3) end of flowering; (4) and (5) fruit size up to 10 mm. The incidence of disease was observed about a week after the last treatment. The results of this study are below in Table I.

A 40% suspension concentrate formulation was used as the source of 3-(difluoromethyl)-1-methyl-N-[(3R)-1,1,3-trimethyl-2,3-dihydroinden-4-yl]pyrazole-4-carboxamide (available from Sumitomo Chemical Company, Tokyo, Japan).

Regulaid® is a nonionic surfactant and was used as the source of the 2-butoxyethanol, poloxalene, and monopropylene glycol surfactant (Regulaid is available from and a registered trademark of KALO, Inc). Regulaid® contains about 90.6% of 2-butoxyethanol, poloxalene, and monopropylene glycol.

Sovran® was used as the source of kresoxim-methyl (available from and a registered trademark of BASF Corporation).

Fontelis® was used as the source of penthiopyrad (available from and a registered trademark of E.I. du Pont).

Slygard® 309 was used as the source of a mixture of 3-(3-hydroxypropyl)-heptamethyltrisiloxane-ethoxylated acetate, polyethylene glycol monallyl acetate and polyethylene glycol diacetate silicone containing surfactant (available from and a registered trademark of Wilbur-Ellis Company). Slygard® 309 contains 100% of the mixture of surfactants.

TABLE 1

| Treatment | Rate (grams active/ha) | % Control |
|---|---|---|
| Control | n/a | 0 |
| 3-(Difluoromethyl)-1-methyl-N-[(3R)-1,1,3-trimethyl-2,3-dihydroinden-4-yl]pyrazole-4-carboxamide | 50 | 67 |

TABLE 1-continued

| Treatment | Rate (grams active/ha) | % Control |
|---|---|---|
| 3-(Difluoromethyl)-1-methyl-N-[(3R)-1,1,3-trimethyl-2,3-dihydroinden-4-yl]pyrazole-4-carboxamide + silicone surfactant | 50<br>584 mL/ha | 96 |
| 3-(Difluoromethyl)-1-methyl-N-[(3R)-1,1,3-trimethyl-2,3-dihydroinden-4-yl]pyrazole-4-carboxamide + 2-butoxyethanol, poloxalene, and monopropylene glycol surfactant | 50<br>0.125% v/v | 71 |
| 3-(Difluoromethyl)-1-methyl-N-[(3R)-1,1,3-trimethyl-2,3-dihydroinden-4-yl]pyrazole-4-carboxamide + methylated seed oil | 50<br>0.06% v/v | 69 |
| Kresoxim-methyl | 224 | 63 |
| Penthiopyrad | 234 | 71 |

Applicant did not expect for the 3-(difluoromethyl)-1-methyl-N-[(3R)-1,1,3-trimethyl-2,3-dihydroinden-4-yl]pyrazole-4-carboxamide and silicone containing surfactant treatment to provide 96% control of apple powdery mildew. Other adjuvants, such as the 2-butoxyethanol, poloxalene, and monopropylene glycol surfactant, provided only 71% control. Further, the 3-(difluoromethyl)-1-methyl-N-[(3R)-1,1,3-trimethyl-2,3-dihydroinden-4-yl]pyrazole-4-carboxamide and silicone containing surfactant treatment provided better control than the commercial formulations that included kresoxim-methyl and penthiopyrad. In addition, no phytotoxicity was observed on the trees treated with 3-(difluoromethyl)-1-methyl-N-[(3R)-1,1,3-trimethyl-2,3-dihydroinden-4-yl]pyrazole-4-carboxamide and the silicone containing surfactant.

Example 2

Applicant conducted the following study to determine the effect of a 3-(difluoromethyl)-1-methyl-N-[(3R)-1,1,3-trimethyl-2,3-dihydroinden-4-yl]pyrazole-4-carboxamide foliar applications on fungal infections in apple trees.

Apples, jonagold variety, that were about 10 years old were used in this study. The trees were spaced about 3 meters apart in about 5 meter rows. The trees were sprayed with a backpack sprayer with a hollow cone nozzle. About 300 liters per hectare was used for each treatment. The trees were treated seven times from 10-14 day intervals starting on Mar. 30, 2015. At the time of treatment, the trees were at the following stages of development: (1) mouse-ear stage: green leaf tips 10 mm above bud scales; first leaves separating; (2) most flowers with petals forming a hollow ball; (3) full flowering; at least 50% of flowers open; (4) end of flowering: all petals fallen (5) fruit size up to 20 mm; (6) Fruit diameter up to 40 mm; fruit erect (T-stage: underside of fruit and stalk); (7) Fruit about half final size. Pest incidence, pest severity, and fruit finish were measured. The results of this study are below in Tables 2-4.

SYL-COAT™ was used as the source of polyether-polymethylsiloxane-copolymer and polyether silicone containing surfactant (available from Wilbur-Ellis Company).

TABLE 2

| Incidence of Apple Powdery Mildew (%) | Application Rate | 8 days after 4th treatment | 2 days after 5th treatment | 3 days after 6th treatment |
|---|---|---|---|---|
| Control | n/a | 21.2500 a | 85.4925 a | 89.1689 a |
| Penthiopyrad | 234 g/ha | 7.5000 bc | 1.4675 cd | 2.5965 ef |

TABLE 2-continued

| Incidence of Apple Powdery Mildew (%) | Application Rate | 8 days after 4th treatment | 2 days after 5th treatment | 3 days after 6th treatment |
|---|---|---|---|---|
| Kresoxim-methyl | 224 g/ha | 8.7500 bc | 3.4874 cd | 12.0332 cd |
| 3-(difluoromethyl)-1-methyl-N-[(3R)-1,1,3-trimethyl-2,3-dihydroinden-4-yl]pyrazole-4-carboxamide | 50 g/ha | 13.0000 b | 11.5303 bc | 20.4938 c |
| 3-(difluoromethyl)-1-methyl-N-[(3R)-1,1,3-trimethyl-2,3-dihydroinden-4-yl]pyrazole-4-carboxamide + 2-butoxyethanol, poloxalene, and monopropylene glycol surfactant | 50 g/ha 0.125% v/v | 11.7500 b | 2.5436 cd | 7.4192 de |
| 3-(difluoromethyl)-1-methyl-N-[(3R)-1,1,3-trimethyl-2,3-dihydroinden-4-yl]pyrazole-4-carboxamide + silicone surfactant | 50 g/ha 8 fl oz/a | 2.2500 c | 0.0824 d | 0.5502 f |
| silicone surfactant | 8 fl oz/a | 12.0000 b | 29.5327 b | 53.7549 b |
| Penthiopyrad + silicone surfactant | 234 g/ha 8 fl oz/a | 2.7500 c | .3252 cd | 0.3048 f |

*Values with a common letter are not significantly different according to the analysis of variance and least significant difference at P = 0.05.

TABLE 3

| Severity of Apple Powdery Mildew (%) | Application Rate | 2 days after 5th treatment | 3 days after 6th treatment | 9 days after 7th treatment |
|---|---|---|---|---|
| Control | n/a | 12.5391 a | 20.4397 a | 35.2449 a |
| Penthiopyrad | 234 g/ha | 0.6379 cd | 0.7932 d | 7.8439 c |
| Kresoxim-methyl | 224 g/ha | 0.8465 cd | 2.9013 c | 9.0294 bc |
| 3-(difluoromethyl)-1-methyl-N-[(3R)-1,1,3-trimethyl-2,3-dihydroinden-4-yl]pyrazole-4-carboxamide | 50 g/ha | 1.6836 bc | 4.4196 c | 11.5331 bc |
| 3-(difluoromethyl)-1-methyl-N-[(3R)-1,1,3-trimethyl-2,3-dihydroinden-4-yl]pyrazole-4-carboxamide + 2-butoxyethanol, poloxalene, and monopropylene glycol surfactant | 50 g/ha 0.125 % v/v | 0.6368 cd | 1.5964 d | 11.0086 bc |
| 3-(difluoromethyl)-1-methyl-N-[(3R)-1,1,3-trimethyl-2,3-dihydroinden-4-yl]pyrazole-4-carboxamide + silicone surfactant | 50 g/ha 8 fl oz/a | 0.0937 d | 0.1962 e | 1.1443 d |
| silicone surfactant | 8 fl oz/a | 3.6230 b | 9.5287 b | 15.9439 b |
| Penthiopyrad + silicone surfactant | 234 g/ha 8 fl oz/a | 0.5194 d | 0.1438 e | 1.2505 d |

*Values with a common letter are not significantly different according to the analysis of variance and least significant difference at P = 0.05.

TABLE 4

| Fruit Finish Quality (0 lowest-10 highest) | Application Rate | 80 days after 7th treatment |
|---|---|---|
| Control | n/a | 6.0000 c |
| Penthiopyrad | 234 g/ha | 8.0000 b |
| Kresoxim-methyl | 224 g/ha | 8.2500 b |
| 3-(difluoromethyl)-1-methyl-N-[(3R)-1,1,3-trimethyl-2,3-dihydroinden-4-yl]pyrazole-4-carboxamide | 50 g/ha | 7.5000 b |
| 3-(difluoromethyl)-1-methyl-N-[(3R)-1,1,3-trimethyl-2,3-dihydroinden-4-yl]pyrazole-4-carboxamide + 2-butoxyethanol, poloxalene, and monopropylene glycol surfactant | 50 g/ha 0.125% v/v | 9.5000 a |
| 3-(difluoromethyl)-1-methyl-N-[(3R)-1,1,3-trimethyl-2,3-dihydroinden-4-yl]pyrazole-4-carboxamide + silicone surfactant | 50 g/ha 8 fl oz/a | 9.5000 a |
| silicone surfactant | 8 fl oz/a | 6.2500 c |
| Penthiopyrad + silicone surfactant | 234 g/ha 8 fl oz/a | 9.5000 a |

*Values with a common letter are not significantly different according to the analysis of variance and least significant difference at P = 0.05.

Applicant unexpectedly found that 3-(difluoromethyl)-1-methyl-N-[(3R)-1,1,3-trimethyl-2,3-dihydroinden-4-yl]pyrazole-4-carboxamide and a silicone containing surfactant provided significantly improved control of apple powdery mildew over either 3-(difluoromethyl)-1-methyl-N-[(3R)-1,1,3-trimethyl-2,3-dihydroinden-4-yl]pyrazole-4-carboxamide or the silicone surfactant alone. See Table 2 (incidence of apple powdery mildew) and Table 3 (severity of apple powdery mildew). This amount of control was unexpected because other adjuvants such as 2-butoxyethanol, poloxalene, and monopropylene glycol surfactant did not significantly improve the control of apple powdery mildew exhibited by 3-(difluoromethyl)-1-methyl-N-[(3R)-1,1,3-trimethyl-2,3-dihydroinden-4-yl]pyrazole-4-carboxamide alone in most applications. Further, penthiopyrad and a silicone containing surfactant did not significantly improve the control of apple powdery mildew exhibited by penthiopyrad alone in most applications. Additionally, applicants unexpectedly found that 3-(difluoromethyl)-1-methyl-N-[(3R)-1,1,3-trimethyl-2,3-dihydroinden-4-yl]pyrazole-4-carboxamide and a silicone containing surfactant provided significantly improved fruit finish quality over either 3-(difluoromethyl)-1-methyl-N-[(3R)-1,1,3-trimethyl-2,3-dihydroinden-4-yl]pyrazole-4-carboxamide or the silicone surfactant alone demonstrating long-lasting control. See Table 4. Finally, Applicant found that a 3-(difluoromethyl)-1-methyl-N-[(3R)-1,1,3-trimethyl-2,3-dihydroinden-4-yl]pyrazole-4-carboxamide and silicone containing surfactant treatment provided better control of apple powdery mildew than the commercial formulations that included kresoximmethyl and penthiopyrad. See Tables 2 and 3. In addition, no phytotoxicity was observed on the trees treated with 3-(difluoromethyl)-1-methyl-N-[(3R)-1,1,3-trimethyl-2,3-dihydroinden-4-yl]pyrazole-4-carboxamide and the silicone containing surfactant.

The invention claimed is:

1. A method of controlling apple powdery mildew comprising applying an effective amount of a silicone containing surfactant and 3-(difluoromethyl)-1-methyl-N-[(3R)-1,1,3-trimethyl-2,3-dihydroinden-4-yl]pyrazole-4-carboxamide to an apple tree.

2. The method of claim 1 wherein the effective amount of 3-(difluoromethyl)-1-methyl-N-[(3R)-1,1,3-trimethyl-2,3-dihydroinden-4-yl]pyrazole-4-carboxamide is from about 0.0001 to about 1,000 grams per hectare.

3. The method of claim 2 wherein the effective amount of 3-(difluoromethyl)-1-methyl-N-[(3R)-1,1,3-trimethyl-2,3-dihydroinden-4-yl]pyrazole-4-carboxamide is from about 0.001 to about 250 grams per hectare.

4. The method of claim 1 wherein the silicone containing surfactant is selected from the group consisting of: a mixture of 3-(3-hydroxypropyl)-heptamethyltrisiloxane-ethoxylated acetate, polyethylene glycol monallyl acetate and polyethylene glycol diacetate; modified polytrisiloxanes; polyalkyleneoxide modified heptamethyltrisiloxanes; a mixture of silicone-polyether copolymers, propylene glycol, and dimethylpolysiloxane; alcohol ethoxylates; polyether-polymethylsiloxane-copolymer and polyether; and combinations thereof.

5. The method of claim 4 wherein the silicone containing surfactant is a mixture of 3-(3-hydroxypropyl)-heptamethyltrisiloxane-ethoxylated acetate, polyethylene glycol monallyl acetate and polyethylene glycol diacetate.

6. The method of claim 1 wherein the amount of silicone containing surfactant is from about 100 to about 1,000 milliliters per hectare.

7. The method of claim 6 wherein the amount of silicone containing surfactant is from about 250 to about 750 milliliters per hectare.

8. The method of claim 1 wherein the apple tree is selected from the group consisting of braeburn, cameo, cortland, crabapple, empire, Fuji, flowering crabapple, gala, ginger gold, golden delicious, granny smith, honeycrisp, jonagold, jonathan, McIntosh, mutsu, nittany, pink lady, rome, idared, red delicious, stayman, winesap, and york.

9. The method of claim 1 wherein the 3-(difluoromethyl)-1-methyl-N-[(3R)-1,1,3-trimethyl-2,3-dihydroinden-4-yl]pyrazole-4-carboxamide is mixed with a solvent prior to application.

10. The method of claim 9 wherein the solvent is water.

11. The method of claim 1 wherein the 3-(difluoromethyl)-1-methyl-N-[(3R)-1,1,3-trimethyl-2,3-dihydroinden-4-yl]pyrazole-4-carboxamide and silicone containing surfactant are mixed with a triazole fungicide.

12. The method of claim 11 wherein the triazole fungicide is metconazole.

13. The method of claim 1 wherein the 3-(difluoromethyl)-1-methyl-N-[(3R)-1,1,3-trimethyl-2,3-dihydroinden-4-yl]pyrazole-4-carboxamide and silicone containing surfactant are mixed with an inhibitor of succinate-dehydrogenase.

14. The method of claim 13 wherein the inhibitor of succinate-dehydrogenase is selected from the group consisting of penflufen, isopyrazam, bixafen, sedaxane, fluxapyroxad, fluopyram, penthiopyrad, boscalid, N-[1-(2,4-dichlohenyl)-1-methoxypropan-2-yl]-3-(difluoromethyl)-1-methyl-1H-pyrazole-4-carboxamide, N[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(dichlormethylen)-1,2,3,4-tetrahydro-1,4-methanonaphthalen-5-yl]-3-(difluormethyl)-1-methyl-1H-pyrazol-4-carboxamid.

15. The method of claim 1 wherein the 3-(difluoromethyl)-1-methyl-N-[(3R)-1,1,3-trimethyl-2,3-dihydroinden-4-yl]pyrazole-4-carboxamide and silicone containing surfactant are mixed with an insecticide.

16. The method of claim 15 wherein the insecticide is a neonicotinoid.

17. The method of claim 16 wherein the neonicotinoid is selected from the group consisting of clothianidin, imidacloprid, thiacloprid, dinotefuran, acetamiprid, nitenpyram and thiamethoxam.

18. The method of claim 1 wherein the 3-(difluoromethyl)-1-methyl-N-[(3R)-1,1,3-trimethyl-2,3-dihydroinden-4-yl]pyrazole-4-carboxamide and silicone containing surfactant are mixed with a strobilurin.

19. The method of claim 18 wherein the strobilurin is selected from the group consisting of picoxystrobin, pyraclostrobin, dimoxystrobin, metominostrobin, azoxystrobin, trifloxystrobin, fluoxastrobin, mandestrobin and orysastrobin.

20. A composition for controlling apple powdery mildew comprising from about 0.00027% to about 0.0007% v/v of a silicone containing surfactant, about 0.000013% to about 0.00008% w/v 3-(difluoromethyl)-1-methyl-N-[(3R)-1,1,3-trimethyl-2,3-dihydroinden-4-yl]pyrazole-4-carboxamide and from about 99.99922% to about 99.99972% v/v water, wherein w/v denotes weight by total volume and v/v denotes volume by total volume.

* * * * *